(12) United States Patent
Hyun et al.

(10) Patent No.: US 8,944,050 B2
(45) Date of Patent: Feb. 3, 2015

(54) INHALATION AIRFLOW REGULATION DEVICES AND METHODS OF USING THE SAME

(75) Inventors: Sinjae Hyun, Macon, GA (US); Melissa Erin Sindelar, Martinez, GA (US); Haley Marie Swearingen, Evans, GA (US); Bennett Welch, Verona, WI (US)

(73) Assignee: The Corporation of Mercer University, Macon, GA (US)

( * ) Notice: Subject to any disclaimer, the term of this patent is extended or adjusted under 35 U.S.C. 154(b) by 703 days.

(21) Appl. No.: 13/209,272

(22) Filed: Aug. 12, 2011

(65) Prior Publication Data
US 2012/0048268 A1 Mar. 1, 2012

Related U.S. Application Data

(60) Provisional application No. 61/373,728, filed on Aug. 13, 2010.

(51) Int. Cl.
*A61M 15/00* (2006.01)
(52) U.S. Cl.
CPC ........... *A61M 15/009* (2013.01); *A61M 15/002* (2013.01); *A61M 15/0021* (2013.01)
USPC .............................. 128/203.12; 128/200.24

(58) Field of Classification Search
CPC .......... A61M 5/14224; A61M 11/005; A61M 15/0085; A61M 1/0084; A61M 15/0086; A61M 1/107; A61M 1/3663
See application file for complete search history.

(56) References Cited

U.S. PATENT DOCUMENTS

| | | | | |
|---|---|---|---|---|
| 3,664,337 | A * | 5/1972 | Lindsey et al. | 128/200.18 |
| 3,826,255 | A * | 7/1974 | Havstad et al. | 128/200.18 |
| 4,446,863 | A * | 5/1984 | Rubin et al. | 128/204.18 |
| 5,617,844 | A * | 4/1997 | King | 128/200.18 |
| 6,070,573 | A * | 6/2000 | Howe et al. | 128/200.14 |
| 6,076,519 | A * | 6/2000 | Johnson | 128/200.14 |
| 6,679,250 | B2 * | 1/2004 | Walker et al. | 128/200.21 |
| 6,761,729 | B2 * | 7/2004 | Babaev | 607/89 |
| 6,929,003 | B2 * | 8/2005 | Blacker et al. | 128/203.12 |
| 2006/0231090 | A1 * | 10/2006 | King | 128/200.14 |

* cited by examiner

*Primary Examiner* — Tan-Uyen (Jackie) T Ho
*Assistant Examiner* — Eric Bryant
(74) *Attorney, Agent, or Firm* — Withers & Keys, LLC (57) ABSTRACT

Inhalation airflow regulation devices and inhalers are disclosed. Methods of making and using inhalation airflow regulation devices are also disclosed.

19 Claims, 7 Drawing Sheets

INHALATION AIRFLOW REGULATION DEVICES AND METHODS OF USING THE SAME

CROSS-REFERENCE TO RELATED APPLICATIONS

This patent application claims the benefit of priority to U.S. Provisional Patent Application Ser. No. 61/373,728 filed on Aug. 13, 2010 and entitled "INHALATION AIRFLOW REGULATION DEVICES AND METHODS OF USING THE SAME," the subject matter of which is hereby incorporated by reference in its entirety.

TECHNICAL FIELD

The present invention relates to inhalation airflow regulation devices, and methods of making and using inhalation airflow regulation devices.

BACKGROUND

Asthma is a disease that constricts the bronchial airways and limits a person's ability to breathe. This condition is a constant problem for many asthma sufferers, frequently causing them to inhale more rapidly than a person who does not have the disease. However, during an asthma attack, a person will begin gasping for breath, so his or her breathing pattern becomes very rapid.

Air is sharply accelerated when entering the mouth and passing through the trachea on its way to the lungs. In order to calm this attack, an asthma inhaler that contains corticosteroids and/or bronchodilators that reduce the inflammation in the airways is used so that normal breathing may resume. The problem is that much of this medication (about 85-95%) is deposited in the mouth, throat, and trachea, especially in the oropharyngeal region, instead of the lungs.

Efforts continue to develop inhalers and inhaler components that do not have some of the problems associated with known inhalers. In particular, efforts continue to develop inhalers and inhaler components that reduce the amount of mouth/throat particle deposition (MTPD), and consequently, the amount of wasted drug.

SUMMARY

The present invention continues the effort to develop inhalers and inhaler components by the discovery of inhalation airflow regulation devices that provide controlled air flow through an inhaler so as to increase the amount of medication reaching the user's lungs as oppose to being deposited in the user's mouth, the oropharyngeal region, and trachea region.

In one exemplary embodiment, the inhalation airflow regulation device of the present invention comprises a tubular member having a first end, an opposite second end, and an air flow cross-sectional area between the first end and the opposite second end; an air outlet positioned proximate the first end; a first air inlet positioned proximate the second end; and an air flow regulating member positioned along the tubular member, the air flow regulating member comprising one or more coplanar sheets of material (i) positioned substantially perpendicular to two-way air flow thru the tubular member at a first location within the tubular member, (ii) secured to the tubular member so as to block a portion, but not all, of the air flow cross-sectional area so as to allow two-way air flow thru the tubular member at the first location, and (iii) secured to the tubular member so as to move toward the first end within the tubular member in response to a threshold amount of an inhalation force applied thereon.

In another exemplary embodiment, the inhalation airflow regulation device of the present invention comprises a tubular member having a first end and an opposite second end; a mouthpiece positioned proximate the first end; a first air inlet positioned proximate the second end; a medication inlet positioned along the tubular member between the mouthpiece and the first air inlet; and an air flow regulating member positioned along the tubular member between the medication inlet and the first air inlet, the air flow regulating member regulating air flow that passes thru the tubular member and by the medication inlet.

In yet another exemplary embodiment, the inhalation airflow regulation device of the present invention comprises a tubular member having a first end and an opposite second end; a mouthpiece positioned proximate the first end; a first air inlet positioned proximate the second end; a medication inlet positioned along the tubular member between the mouthpiece and the first air inlet; and an air flow regulating member positioned along the tubular member between the medication inlet and the first air inlet, the air flow regulating member comprising a sheet of material (i) positioned substantially perpendicular to a direction of air flow thru the tubular member, (ii) secured to the tubular member so as to block at least a portion of an air flow cross-sectional area of the tubular member, and (iii) secured to the tubular member so as to move within the tubular member in response to a threshold amount of an inhalation force applied thereon.

In yet another exemplary embodiment, the inhalation airflow regulation device of the present invention comprises a tubular member having a first end, an opposite second end, and an air flow cross-sectional area between the first end and the opposite second end; a mouthpiece positioned proximate the first end; a first air inlet positioned proximate the second end; a medication inlet positioned along the tubular member; and an air flow regulating member positioned along the tubular member, the air flow regulating member comprising a sheet of material (i) positioned substantially perpendicular to two-way air flow thru the tubular member at a first location within the tubular member, (ii) secured to the tubular member so as to block a portion, but not all, of the air flow cross-sectional area to as to allow two-way air flow thru the tubular member at the first location, and (iii) secured to the tubular member so as to move within the tubular member in response to a threshold amount of an inhalation force applied thereon.

Any of the disclosed inhalation airflow regulation devices may be used in combination with a medication canister and/or other components to form an inhaler. In one exemplary embodiment, the disclosed inhalation airflow regulation device is used in combination with at least one medication canister to form an inhaler. In some cases, multiple medication canisters and at least one disclosed inhalation airflow regulation device may be combined to form an inhaler kit. In another exemplary embodiment, the disclosed inhalation airflow regulation device is used in combination with at least one medication canister and a medication canister holding device to form an inhaler kit. In some cases, multiple medication canisters, at least one medication canister holding device, and at least one disclosed inhalation airflow regulation device may be combined to form a kit.

The present invention is also directed to methods of making inhalation airflow regulation devices. In one exemplary embodiment, the method of making an inhalation airflow regulation device comprises forming a tubular member having a first end, an opposite second end, and an air flow cross-sectional area between the first end and the opposite second end, an air outlet positioned proximate the first end, and a first air inlet positioned proximate the second end; and positioning an air flow regulating member along the tubular member, the air flow regulating member comprising one or more coplanar sheets of material (i) positioned substantially perpendicular to two-way air flow thru the tubular member at a first location within the tubular member, (ii) secured to the tubular member so as to block a portion, but not all, of the air flow cross-sectional area so as to allow two-way air flow thru the tubular member at the first location, and (iii) secured to the tubular member so as to move toward the first end within the tubular member in response to a threshold amount of an inhalation force applied thereon.

In another exemplary embodiment, the method of making an inhalation airflow regulation device comprises forming a tubular member having a first end and an opposite second end, a mouthpiece positioned proximate the first end, a first air inlet positioned proximate the second end, and a medication inlet positioned along the tubular member between the mouthpiece and the first air inlet; and positioning an air flow regulating member along the tubular member between the medication inlet and the first air inlet, the air flow regulating member regulating air flow that passes thru the tubular member and by the medication inlet.

In yet another exemplary embodiment, the method of making an inhalation airflow regulation device comprises forming a tubular member having a first end and an opposite second end, a mouthpiece positioned proximate the first end, a first air inlet positioned proximate the second end, and a medication inlet positioned along the tubular member between the mouthpiece and the first air inlet; and positioning an air flow regulating member along the tubular member between the medication inlet and the first air inlet, the air flow regulating member comprising a sheet of material (i) positioned substantially perpendicular to a direction of air flow thru the tubular member, (ii) secured to the tubular member so as to block at least a portion of an air flow cross-sectional area of the tubular member, and (iii) secured to the tubular member so as to move within the tubular member in response to a threshold amount of an inhalation force applied thereon.

In yet another exemplary embodiment, the method of making an inhalation airflow regulation device comprises forming a tubular member having a first end, an opposite second end, an air flow cross-sectional area between the first end and the opposite second end, a mouthpiece positioned proximate the first end, a first air inlet positioned proximate the second end, and a medication inlet positioned along the tubular member; and positioning an air flow regulating member along the tubular member, the air flow regulating member comprising a sheet of material (i) positioned substantially perpendicular to two-way air flow thru the tubular member at a first location within the tubular member, (ii) secured to the tubular member so as to block a portion, but not all, of the air flow cross-sectional area to as to allow two-way air flow thru the tubular member at the first location, and (iii) secured to the tubular member so as to move within the tubular member in response to a threshold amount of an inhalation force applied thereon.

The exemplary methods of making an inhalation airflow regulation device may further comprise one or more additional steps. Suitable additional steps include, but are not limited to, cutting one or more air flow regulating members from a sheet of material wherein each air flow regulating member has a desired shape/configuration; attaching the air flow regulating member to an inner surface of the tubular member; attaching the air flow regulating member to an edge surface of the tubular member;

The present invention is further directed to methods of using inhalation airflow regulation devices. In one exemplary embodiment, the method of using an inhalation airflow regulation device comprises optionally combining the inhalation airflow regulation device with one or more inhaler components; and applying a threshold amount of an inhalation force onto an air flow regulating member positioned along a tubular member of the inhalation airflow regulation device so as to regulate air flow through the inhalation airflow regulation device.

In another exemplary embodiment, the method of using an inhalation airflow regulation device comprises optionally combining the inhalation airflow regulation device with one or more inhaler components; and applying a threshold amount of an inhalation force onto an air flow regulating member positioned along a tubular member between a medication inlet and a first air inlet of the inhalation airflow regulation device, the air flow regulating member regulating air flow that passes thru the tubular member and by the medication inlet with minimal (if any) loss of injected inhalation medication due to early deposition on the user's mouth, the oropharyngeal region, and trachea region.

In another exemplary embodiment, the method of using an inhalation airflow regulation device comprises positioning the inhalation airflow regulation device proximate a user's mouth, the inhalation airflow regulation device comprising a tubular member having a first end and an opposite second end, a mouthpiece positioned proximate the first end, a first air inlet positioned proximate the second end, a medication inlet positioned along the tubular member between the mouthpiece and the first air inlet, and an air flow regulating member along the tubular member between the medication inlet and the first air inlet, the air flow regulating member comprising a sheet of material (i) positioned substantially perpendicular to a direction of air flow thru the tubular member, (ii) secured to the tubular member so as to block at least a portion of an air flow cross-sectional area of the tubular member, and (iii) secured to the tubular member so as to move within the tubular member in response to a threshold amount of an inhalation force applied thereon; and inhaling so as to apply the threshold amount of inhalation force onto the air flow regulating member.

In yet another exemplary embodiment, the method of using an inhalation airflow regulation device comprises positioning the inhalation airflow regulation device proximate a user's mouth, the inhalation airflow regulation device comprising a tubular member having a first end, an opposite second end, an air flow cross-sectional area between the first end and the opposite second end, a mouthpiece positioned proximate the first end, a first air inlet positioned proximate the second end, a medication inlet positioned along the tubular member, and an air flow regulating member along the tubular member, the air flow regulating member comprising a sheet of material (i) positioned substantially perpendicular to two-way air flow thru the tubular member at a first location within the tubular member, (ii) secured to the tubular member so as to block a portion, but not all, of the air flow cross-sectional area to as to allow two-way air flow thru the tubular member at the first location, and (iii) secured to the tubular member so as to move within the tubular member in response to a threshold amount of an inhalation force applied thereon; and inhaling so as to apply the threshold amount of inhalation force onto the air flow regulating member. Desirably, the threshold amount of inhalation force and the air flow regulating member provide an amount of air flow through the tubular device so as to maximize an amount of medication within the air flow that reaches a user's lungs.

These and other features and advantages of the present invention will become apparent after a review of the following detailed description of the disclosed embodiments and the appended claims.

BRIEF DESCRIPTION OF THE DRAWINGS

The present invention is further described with reference to the appended figures, wherein.

DETAILED DESCRIPTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

Figure 1:
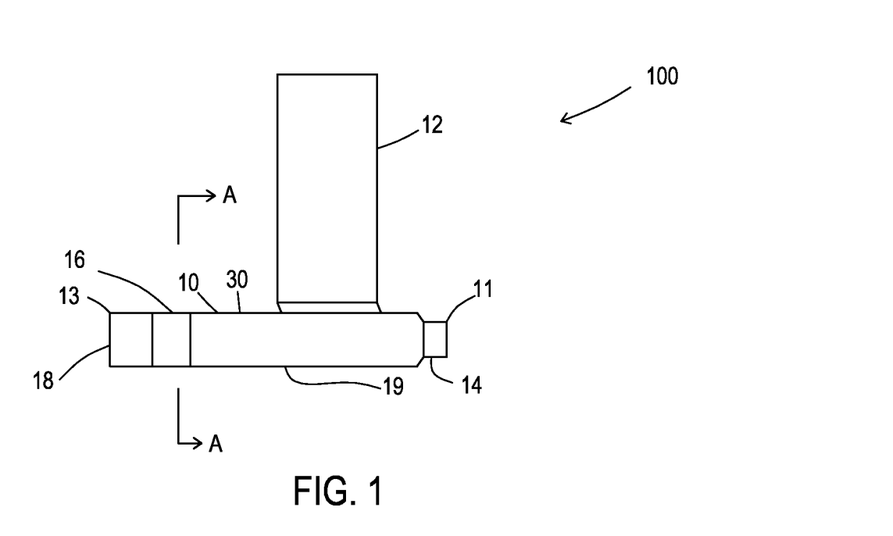
FIG. 1 depicts a side view of an exemplary inhalation airflow regulation device of the present invention.

The present invention is directed to inhalation airflow regulation devices and their use with inhalers. FIG. 1 provides a view of an exemplary inhalation airflow regulation device of the present invention. As shown in FIG. 1, exemplary inhalation airflow regulation device 100 comprises a tubular member 10 having a first end 11 and an opposite second end 13. A mouthpiece 14 is positioned proximate first end 11. Mouthpiece 14 may be an integral part of tubular member 10, as shown in FIG. 1, or a separate part (not shown) that is attachable to tubular member 10 proximate first end 11.

Exemplary tubular member 10 further comprises a first air inlet 18 positioned proximate second end 13. As discussed further below, as a user inhales air or medicated air through tubular member 10, air is pulled into first air inlet 18 and through tubular member 10 toward and through mouthpiece 14. Exemplary tubular member 10 also comprises a region 16 positioned proximate second end 13, and a middle region 19 positioned at an approximate midpoint between first end 11 and opposite second end 13. Exemplary inhalation airflow regulation device 100 may be used in combination with a medicine canister 12 positioned along and connected to tubular member 10 having a first end 11. Typically, medicine canister 12 comprises a pressurized aerosol canister containing a medication. In some embodiments, for example, when exemplary inhalation airflow regulation device 100 is disposable, medicine canister 12 may be permanently attached to tubular member 10. In other embodiments, for example, when exemplary inhalation airflow regulation device 100 is reusable, medicine canister 12 is temporarily attached to and removable from tubular member 10 via a coupling component (see FIGS. 10A-10C).

Figure 2:
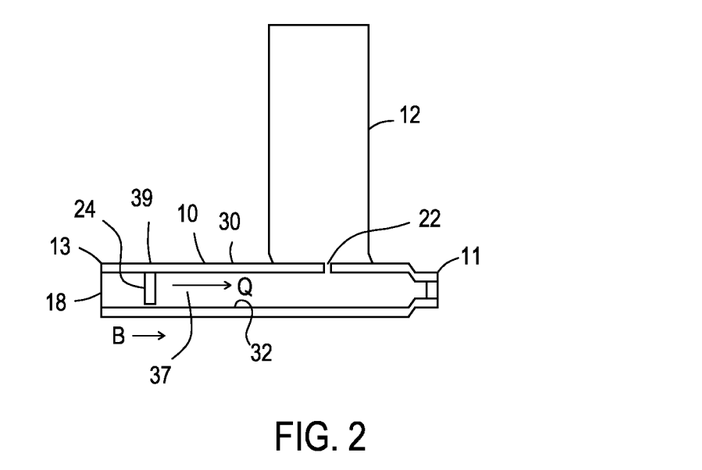
FIG. 2 depicts a cross-sectional view of the exemplary inhalation airflow regulation device shown in FIG. 1 as viewed from the same side view.

FIG. 2 depicts a cross-sectional view of exemplary inhalation airflow regulation device 100 shown in FIG. 1 as viewed from the same side view. As shown in FIG. 2, exemplary inhalation airflow regulation device 100 further comprises an air flow regulating member 24, as well as a medication inlet 22 positioned along tubular member 10. Typically, air flow regulating member 24 is positioned between medication inlet 22 and first air inlet 18. More typically, air flow regulating member 24 is positioned within region 16 as shown in FIG. 2.

Medication inlet 22 enables fluid flow from medicine canister 12 into tubular member 10 thru medication inlet 22. As discussed above and as shown in FIGS. 10A-10C below, a coupling component may be proximate medication inlet 22 so as to couple a removable medicine canister 12 to tubular member 10.

As shown in FIG. 2, exemplary air flow regulating member 24 positioned along tubular member 10 regulates air flow Q passing thru tubular member 10, and, in particular, along inner air flow channel 37 of tubular member 10. Typically, exemplary air flow regulating member 24 regulates air flow Q passing thru inner air flow channel 37 of tubular member 10, by medication inlet 22, and thru mouthpiece 14.

Typically, exemplary air flow regulating member 24 comprises a sheet of elastic material (i) positioned substantially perpendicular to a direction of air flow, as shown by arrow B in FIG. 2, thru inner air flow channel 37 of tubular member 10, (ii) secured to tubular member 10 so as to block at least a portion of an air flow cross-sectional area of tubular member 10, and (iii) secured to tubular member 10 so as to move within tubular member 10 in response to a threshold amount of an inhalation force applied thereon. As shown in FIG. 2, in response to a threshold amount of inhalation force applied to exemplary air flow regulating member 24, at least a portion of exemplary air flow regulating member 24 moves in direction B.

Although exemplary air flow regulating member 24 may comprise any sheet of material, exemplary air flow regulating member 24 typically comprises a sheet of elastomeric material (e.g., neoprene rubber, silicone rubber, etc.). Other suitable materials for forming exemplary air flow regulating member 24 include, but are not limited to a metallic sheet of material, a film, a fiber reinforced film or metal, a fabric, or any combination thereof.

Figure 3:
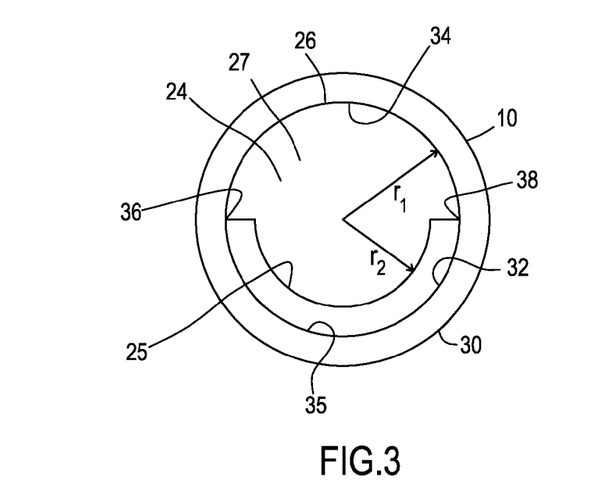
FIG. 3 depicts a cross-sectional view of the exemplary inhalation airflow regulation device shown in FIG. 1 as viewed along the shown exemplary tubular member at line A-A, wherein the exemplary inhalation airflow regulation device comprises a first air flow regulator member positioned along an inner surface of the exemplary tubular member.

As shown in FIGS. 3-4 and 7-8, exemplary air flow regulating member 24 (i) may comprise one or more sheets of material, and (ii) each sheet of material may have a variety of shapes/configurations. In FIG. 3, exemplary air flow regulating member 24 comprises a single sheet of material 27, which may be described as an upper semi-circle having an upper circle radius of $r_1$ joined to a lower semi-circle having a lower circle radius $r_2$, wherein upper semi-circle and lower semi-circle are joined to one another along a shared diameter portion of both circles (i.e., upper circle radius of $r_1$ and lower circle radius $r_2$ originate from the same point).

As shown in FIG. 3, exemplary air flow regulating member 24 comprises single sheet of material 27 having an attached edge 26 and an unattached edge 25. In this exemplary embodiment, each of attached edge 26 and unattached edge 25 extends a length representing about 50% of an overall inner perimeter of tubular member 10 as measured along inner surface 32 of tubular member 10. It should be noted that, in other embodiments, attached edge 26 may extend a length representing as little as about 5% or as much as 100% of an overall inner perimeter of tubular member 10 as measured along inner surface 32 of tubular member 10, and consequently, unattached edge 25 may extend a length representing as little as 0% or as much as about 95% of an overall inner perimeter of tubular member 10 as measured along inner surface 32 of tubular member 10. Typically, attached edge 26 extends a length representing from about 5% to about 50% of an overall inner perimeter of tubular member 10 as measured along inner surface 32 of tubular member 10, while unattached edge 25 extends a length representing from about 50% to about 95% of an overall inner perimeter of tubular member 10 as measured along inner surface 32 of tubular member 10.

As shown in FIG. 3, attached edge 26 of exemplary air flow regulating member 24 extends along inner surface 32 of tubular member 10 from location 36 to location 38 thru attached location 34, while unattached edge 25 extends along inner surface 32 of tubular member 10 from location 36 to location 38 thru unattached location 35. In this exemplary embodiment, exemplary air flow regulating member 24 blocks a portion, but not all, of an air flow cross-sectional area of tubular member 10, wherein the blocked portion is bound by (1) a line extending along inner surface 32 of tubular member 10 from location 36 to location 38 thru attached location 34, and (2) a line extending along unattached edge 25 of exemplary air flow regulating member 24.

As shown in FIG. 3, exemplary air flow regulating member 24 comprises a sheet of material, namely, single sheet of material 27, (i) positioned substantially perpendicular to two-way air flow thru tubular member 10 at a first location 39 within tubular member 10, (ii) secured to tubular member 10 so as to block a portion, but not all, of the air flow cross-sectional area so as to allow two-way air flow thru tubular member 10 at first location 39, and (iii) secured to tubular member 10 so as to move within tubular member 10 in response to a threshold amount of inhalation force applied thereon. Desirably, the threshold amount of inhalation force and exemplary air flow regulating member 24 provide an amount of air flow through tubular device 10 so as to maximize an amount of medication within the air flow that reaches a user's lungs (not shown).

Figure 4:
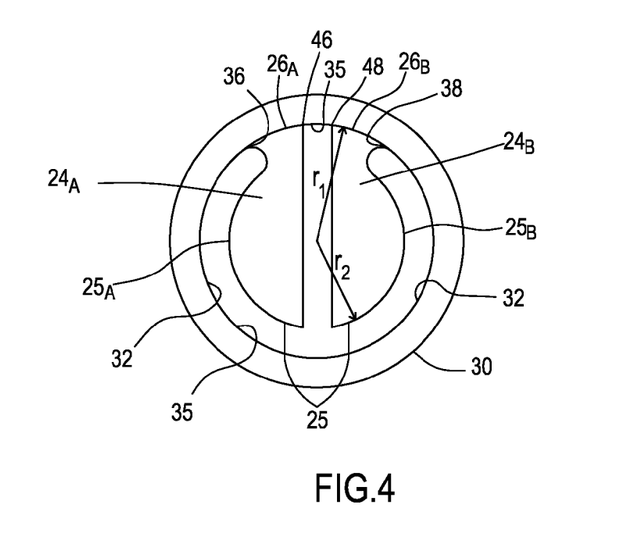
FIG. 4 depicts a cross-sectional view of the exemplary inhalation airflow regulation device shown in FIG. 1 as viewed along the shown exemplary tubular member at line A-A, wherein the exemplary inhalation airflow regulation device comprises a second air flow regulator member positioned along an inner surface of the exemplary tubular member.

As noted above, FIG. 3 depicts a cross-sectional view of exemplary inhalation airflow regulation device 100 shown in FIG. 1 as viewed along exemplary tubular member 10 at line A-A, wherein exemplary inhalation airflow regulation device 100 comprises first exemplary air flow regulator member 24 positioned along inner surface 32 of exemplary tubular member 10. FIG. 4 depicts a cross-sectional view of exemplary inhalation airflow regulation device 100 shown in FIG. 1 as viewed along exemplary tubular member 10 at line A-A, wherein exemplary inhalation airflow regulation device 100 comprises second exemplary air flow regulator member 24 positioned along inner surface 32 of exemplary tubular member 10.

As shown in FIG. 4, exemplary air flow regulating member 24 comprises two separate sheets of material $24_A$ and $24_B$. When viewed together, exemplary air flow regulating member 24 (i.e., sheets of material $24_A$ and $24_B$) may be described as two symmetrical cut-outs from a circle having an outer circle radius of $r_1$ so as to result in separate sheets of material having a semi-circle shape with an inner circle radius $r_2$ and an end portion that extends along inner surface 32 of tubular member 10.

In this exemplary embodiment, attached edges $26_A$ and $26_B$, in combination, extend a length representing about 10% of an overall inner perimeter of tubular member 10 as measured along inner surface 32 of tubular member 10, and unattached edges $25_A$ and $25_B$, in combination, extend a length representing about 90% of an overall inner perimeter of tubular member 10 as measured along inner surface 32 of tubular member 10.

In this exemplary embodiment, exemplary air flow regulating member 24 (i.e., sheets of material $24_A$ and $24_B$) blocks a portion, but not all, of an air flow cross-sectional area of tubular member 10, wherein the blocked portion is bound by (1)(i) a line extending along inner surface 32 of tubular member 10 from location 36 to location 46, and (ii) a line extending along unattached edge $25_A$ of exemplary air flow regulating member 24 back to location 36, and (2)(i) a line extending along inner surface 32 of tubular member 10 from location 38 to location 48, and (ii) a line extending along unattached edge $25_B$ of exemplary air flow regulating member 24 back to location 38.

As shown in FIG. 4, exemplary air flow regulating member 24 may comprise two sheets of material (or any number of separate sheets of material), namely, sheets of material $24_A$ and $24_B$, (i) positioned substantially perpendicular to two-way air flow thru tubular member 10 at a first location 39 within tubular member 10, (ii) secured to tubular member 10 so as to block a portion, but not all, of the air flow cross-sectional area so as to allow two-way air flow thru tubular member 10 at first location 39, and (iii) secured to tubular member 10 so as to move within tubular member 10 in response to a threshold amount of inhalation force applied thereon. Desirably, the threshold amount of inhalation force and exemplary air flow regulating member 24 (i.e., sheets of material $24_A$ and $24_B$) provide an amount of air flow through tubular device 10 so as to maximize an amount of medication within the air flow that reaches a user's lungs (not shown).

As shown in FIGS. 1-4, exemplary air flow regulating member 24 may comprise one or more separate sheets of material (or any number of separate sheets of material, typically, up to about 12 separate sheets) attached to an inner surface (i.e., inner surface 32) of tubular member 10. As shown in FIGS. 5-8, exemplary air flow regulating member 24 may be incorporated into another exemplary tubular member in a manner different than that shown in FIGS. 1-4.

Figure 5:
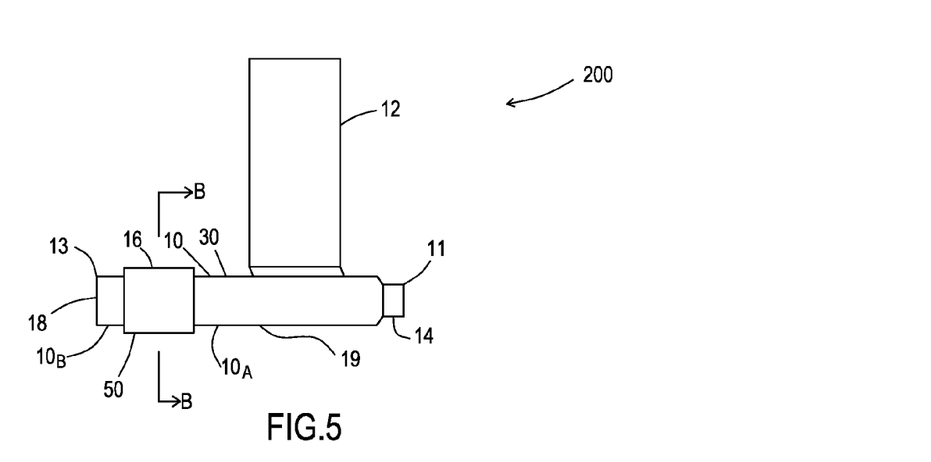
FIG. 5 depicts a side view of another exemplary inhalation airflow regulation device of the present invention.

As shown in FIG. 5, exemplary inhalation airflow regulation device 200 comprises a tubular member 10 comprising two separate tubular member portions $10_A$ and $10_B$. Tubular member portions $10_A$ and $10_B$, in combination, have a first end 11, opposite second end 13, mouthpiece 14 positioned proximate first end 11, and first air inlet 18 positioned proximate second end 13. As discussed above, mouthpiece 14 may be an integral part of tubular member $10_A$, as shown in FIG. 5, or a separate part (not shown) that is attachable to tubular member $10_A$ proximate first end 11. Exemplary inhalation airflow regulation device 200 also comprises an exemplary overlapping tubular member 50 positioned over outer surfaces $30_A$ and $30_B$ proximate end portions of tubular member portions $10_A$ and $10_B$.

Exemplary overlapping tubular member 50 may comprise any component that enables joining of tubular member portion $10_A$ to tubular member portion $10_B$. Suitable components for forming exemplary overlapping tubular member 50 include, but are not limited to, a tubular member (e.g., a piece of tubing or pipe material), a heat-shrinkable film, a film, an elastic band, a metal band, etc.

Figure 6:
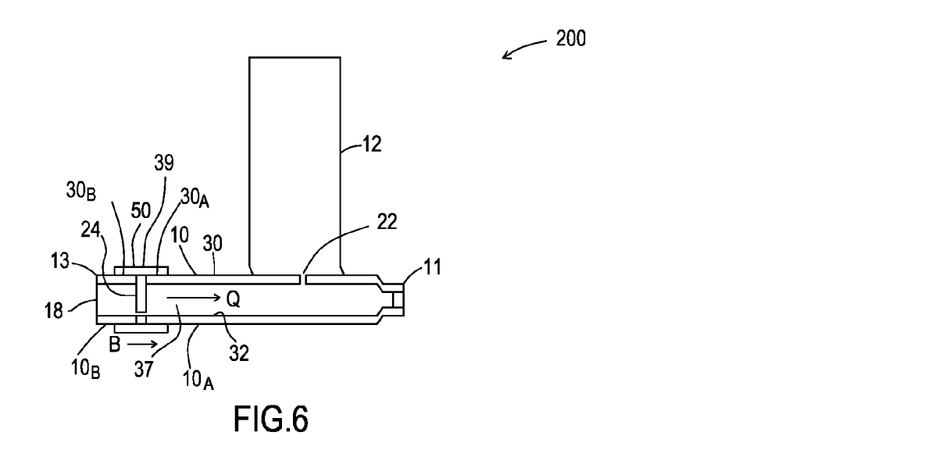
FIG. 6 depicts a cross-sectional view of the exemplary inhalation airflow regulation device shown in FIG. 5 as viewed from the same side view.

FIG. 6 depicts a cross-sectional view of exemplary inhalation airflow regulation device 200 shown in FIG. 5 as viewed along exemplary tubular member 10 at line B-B, wherein exemplary inhalation airflow regulation device 200 comprises first exemplary air flow regulator member 24 positioned along outer edge 30 of exemplary tubular member $10_A$.

Figure 7:
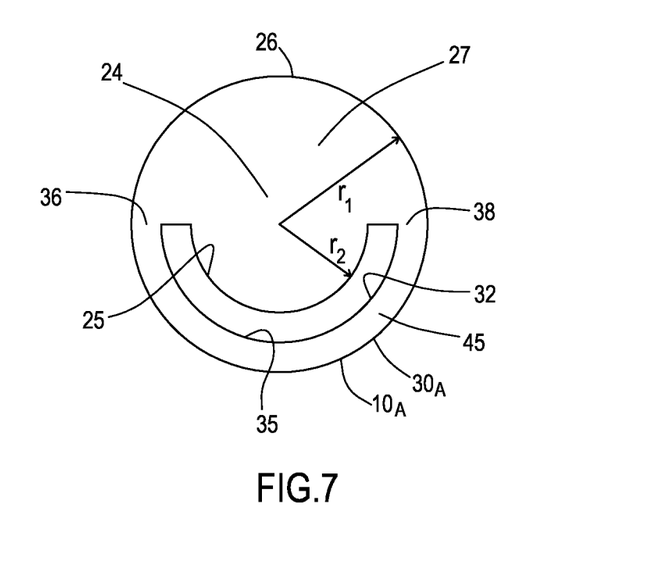
FIG. 7 depicts a cross-sectional view of the exemplary inhalation airflow regulation device shown in FIG. 5 as viewed along the shown exemplary tubular member at line B-B, wherein the exemplary inhalation airflow regulation device comprises the first air flow regulator member positioned along an outer edge of the exemplary tubular member.

FIG. 7 depicts a cross-sectional view of exemplary inhalation airflow regulation device 200 shown in FIG. 5 as viewed along exemplary tubular member 10 at line B-B, wherein exemplary inhalation airflow regulation device 200 comprises first exemplary air flow regulator member 24 (i.e., single sheet of material 27) positioned along outer edge 45 of exemplary tubular member 10 (i.e., along an outer edge of tubular member portion $10_A$). In this exemplary embodiment, upper circle radius $r_1$ of single sheet of material 27 extends to outer surface $30_A$ of tubular member portion $10_A$ such that attached end 26 of single sheet of material 27 is positioned and secured between abutting ends of tubular member portion $10_A$ and tubular member portion $10_B$.

As shown in FIG. 7, attached edge 26 of exemplary air flow regulating member 24 extends along inner surface 32 and outer edge 45 of tubular member $10_A$ from location 36 to location 38, while unattached edge 25 extends along inner surface 32 of tubular member 10 from location 36 to location 38 thru unattached location 35. In this exemplary embodiment, exemplary air flow regulating member 24 blocks a portion, but not all, of an air flow cross-sectional area of tubular member 10, wherein the blocked portion is bound by (1) a line extending along inner surface 32 of tubular member 10 (i.e., along an inner surface of each of tubular member portion $10_A$ and tubular member portion $10_B$) from location 36 to location 38, and (2) a line extending along unattached edge 25 of exemplary air flow regulating member 24.

As shown in FIG. 7, exemplary air flow regulating member 24 comprises a sheet of material, namely, single sheet of material 27, (i) positioned substantially perpendicular to two-way air flow thru tubular member 10 at a first location 39 between tubular member portion $10_A$ and tubular member portion $10_B$, (ii) secured to tubular member 10 (i.e., along an outer edge of at least one or both of tubular member portion $10_A$ and tubular member portion $10_B$) so as to block a portion, but not all, of the air flow cross-sectional area so as to allow two-way air flow thru tubular member 10 at first location 39 (i.e., between tubular member portion $10_A$ and tubular member portion $10_B$), and (iii) secured to tubular member 10 (i.e., along an outer edge of at least one or both of tubular member portion $10_A$ and tubular member portion $10_B$) so as to move within tubular member 10 in response to a threshold amount of inhalation force applied thereon as discussed above.

Figure 8:
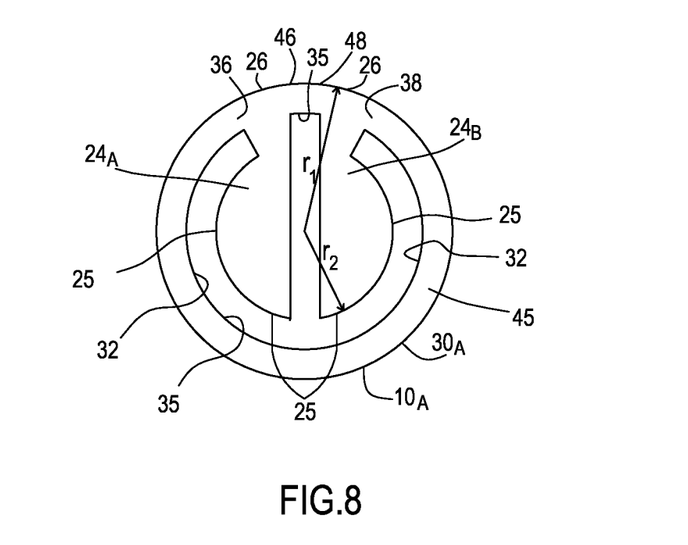
FIG. 8 depicts a cross-sectional view of the exemplary inhalation airflow regulation device shown in FIG. 5 as viewed along the shown exemplary tubular member at line B-B, wherein the exemplary inhalation airflow regulation device comprises the second air flow regulator member positioned along the outer edge of the exemplary tubular member.

FIG. 8 depicts a cross-sectional view of exemplary inhalation airflow regulation device 200 shown in FIG. 5 as viewed along exemplary tubular member 10 at line B-B, wherein exemplary inhalation airflow regulation device 200 comprises the second exemplary air flow regulator member 24 positioned along the outer edge of exemplary tubular member 10 (i.e., along an outer edge of tubular member portion $10_A$). In this exemplary embodiment, each outer circle radius $r_1$ of sheets of material $24_A$ and $24_B$ extends to outer surface $30_A$ of tubular member portion $10_A$ such that attached edges $26_A$ and $26_B$ of sheets of material $24_A$ and $24_B$ are positioned and secured between abutting ends of tubular member portion $10_A$ and tubular member portion $10_B$.

As shown in FIG. 8, attached edges $26_A$ and $26_B$ of exemplary air flow regulating member 24 extend along inner surface 32 and outer edge 45 of tubular member $10_A$ from (i) location 36 to location 46, and (ii) location 38 to location 48. In this exemplary embodiment, exemplary air flow regulating member 24 (i.e., sheets of material $24_A$ and $24_B$) blocks a portion, but not all, of an air flow cross-sectional area of tubular member 10, wherein the blocked portion is bound by (1)(i) a line extending along inner surface 32 of tubular member 10 (i.e., and along an inner surface of both of tubular member portion $10_A$ and tubular member portion $10_B$) from location 36 to location 46, and (ii) a line extending along unattached edge $25_A$ of exemplary air flow regulating member 24 from location 46 back to location 36, and (2)(i) a line extending along inner surface 32 of tubular member 10 (i.e., and along an inner surface of both of tubular member portion $10_A$ and tubular member portion $10_B$) from location 38 to location 48, and (ii) a line extending along unattached edge $25_B$ of exemplary air flow regulating member 24 from location 48 back to location 38.

As shown in FIG. 8, exemplary air flow regulating member 24 comprises sheets of material $24_A$ and $24_B$ (i) positioned substantially perpendicular to two-way air flow thru tubular member 10 at a first location 39 between tubular member portion $10_A$ and tubular member portion $10_B$, (ii) secured to tubular member 10 (i.e., along an outer edge of at least one or both of tubular member portion $10_A$ and tubular member portion $10_B$) so as to block a portion, but not all, of the air flow cross-sectional area so as to allow two-way air flow thru tubular member 10 at first location 39 (i.e., between tubular member portion $10_A$ and tubular member portion $10_B$), and (iii) secured to tubular member 10 (i.e., along an outer edge of at least one or both of tubular member portion $10_A$ and tubular member portion $10_B$) so as to move within tubular member 10 in response to a threshold amount of inhalation force applied thereon as discussed above.

The air flow regulating member 24 (i.e., comprising one or more sheets of material, e.g., sheet 24 or sheets $24_A$ and $24_B$) typically blocks up to about 99% of the air flow cross-sectional area at the first location. In some exemplary embodiments, air flow regulating member 24 (i.e., comprising one or more sheets of material, e.g., sheet 24 or sheets $24_A$ and $24_B$) blocks from about 50% (or about 60%, or about 70%, or about 75%, or about 80%, or about 90%) to about 95% of the air flow cross-sectional area at the first location.

Figure 9:
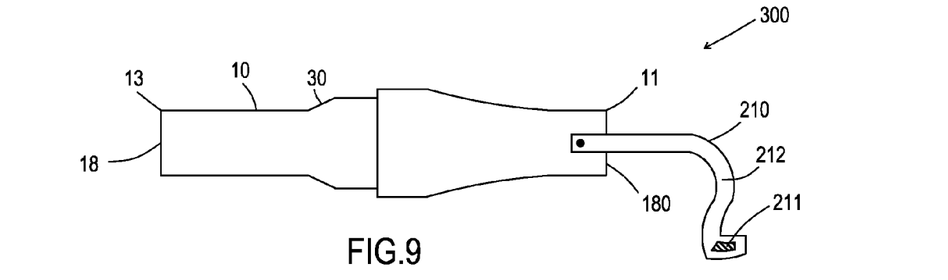
FIG. 9 depicts a side view of another exemplary inhalation airflow regulation device of the present invention.

FIG. 9 depicts a side view of another exemplary inhalation airflow regulation device of the present invention. As shown in FIG. 9, exemplary inhalation airflow regulation device 300 comprises a tubular member 10 comprising a first end 11, opposite second end 13, air outlet 180 positioned proximate first end 11, and first air inlet 18 positioned proximate second end 13. Exemplary inhalation airflow regulation device 300 further comprises a connecting member 210 proximate air outlet 180. Exemplary connecting member 210 is operatively adapted to connect exemplary inhalation airflow regulation device 300 to an air inlet of a separate inhaler component (not shown). For example, the separate inhaler component may comprise an inhaler that does not provide controlled inhalation air flow, but can be modified with exemplary inhalation airflow regulation device 300 so as to be retrofitted to provide controlled inhalation air flow.

It should be understood that exemplary inhalation airflow regulation device 300 may comprise any desired design for air outlet 180 and connecting member 210 as long as exemplary inhalation airflow regulation device 300 is attachable to a separate inhaler component (not shown). For example, air outlet 180 may actually comprise one or more openings within exemplary inhalation airflow regulation device 300 that configurationally match one or more air inlets of the separate inhaler component (not shown). Further, although connecting member 210 is shown as a strap 212 with hook/loop material 211 thereon, connecting member 210 may have any configuration that enables exemplary inhalation airflow regulation device 300 to be attached to the separate inhaler component (not shown) (e.g., mechanical fasteners such as overlapping end components, adhesive tape, an elastic band, a metal band, etc.

Figure 10:
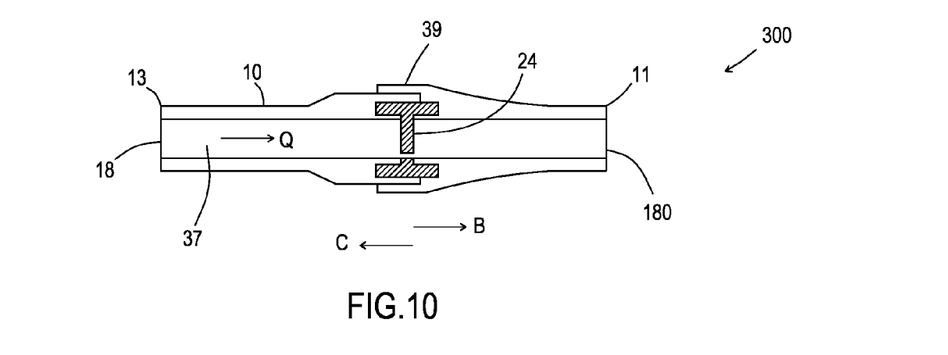
FIG. 10 depicts a cross-sectional view of the exemplary inhalation airflow regulation device shown in FIG. 9 as viewed from the same side view.

FIG. 10 depicts a cross-sectional view of exemplary inhalation airflow regulation device 300 shown in FIG. 9. As shown in FIG. 10, exemplary air flow regulating member 24 is positioned along tubular member 10, and comprises one or more coplanar sheets of material 24 (i) positioned substantially perpendicular to two-way air flow thru tubular member 10 at a first location 39 within tubular member 10, (ii) secured to tubular member 10 so as to block a portion, but not all, of an air flow cross-sectional area so as to allow two-way air flow thru tubular member 10 at first location 39, and (iii) secured to tubular member 10 so as to move toward first end 11 within tubular member 10 (as shown by arrow B) in response to a threshold amount of an inhalation force applied thereon. As with the other disclosed exemplary inhalation airflow regulation devices 100 and 200, air flow regulating member 24 also moves toward second end 13 within tubular member 10 (as shown by arrow C) in response to a threshold amount of an exhalation force applied thereon.

As shown in FIG. 10, exemplary air flow regulating member 24 may be embedded within a material used to form tubular member 10 (e.g., a thermoplastic polymeric material such as polyethylene). Further, exemplary air flow regulating member 24 may have an "I" shape cross-sectional configuration as shown in FIG. 10, while having an "end view" configuration as shown in FIGS. 3-4 and 7-8.

Figure 11:
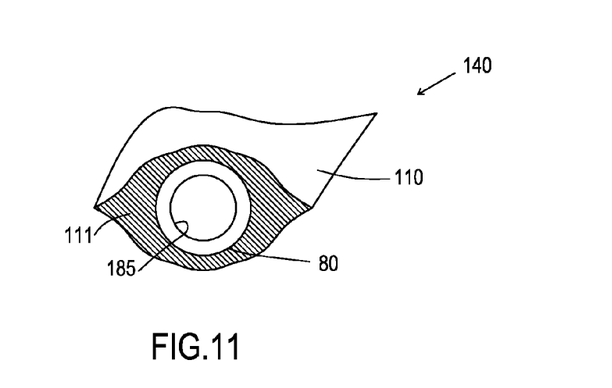
FIG. 11 provides a detailed view of an exemplary mouthpiece suitable for use with the disclosed inhalation airflow regulation devices.

As discussed above, exemplary inhalation airflow regulation devices of the present invention may comprise an integral mouthpiece 14 or a separate mouthpiece 14' that is attachable to tubular member 10 at first end 11. FIG. 11 provides a detailed view of exemplary mouthpiece components 140. As shown in FIG. 11, exemplary mouthpiece components 140 comprise an inlet tube 80 and a mouthpiece cover 110. In some embodiments (i.e., when tubular member 10 comprise an integral mouthpiece 14), inlet tube 80 comprises first end 11 of tubular member 10. In this embodiment, mouthpiece cover 110 slides over first end 11 of tubular member 10. In other embodiments (i.e., a separate mouthpiece 14'), inlet tube 80 essentially comprises an extension of tubular member 10 at first end 11 with mouthpiece cover 110 positioned over inlet tube 80 and, in some embodiments, over a portion of first end 11 of tubular member 10.

Typically, inlet tube 80 comprises a relatively hard plastic material 185, such as an ABS (acrylonitrile-butadiene-styrene) copolymer, while mouthpiece cover 110 comprises a relatively soft material 111 such as a silicone rubber material.

Figure 12A:
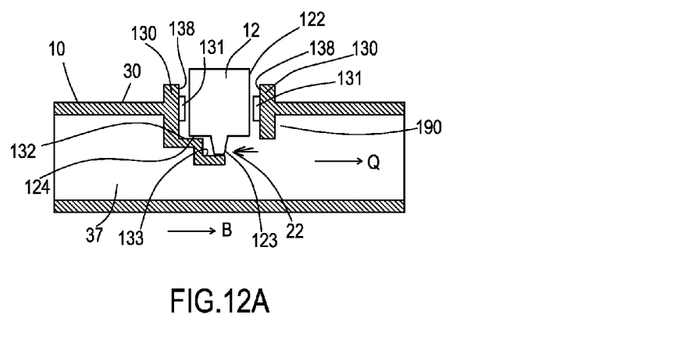
FIGS. 12A-12C provide various views of an exemplary medication canister connector of an exemplary inhalation airflow regulation device.
Figure 12B:
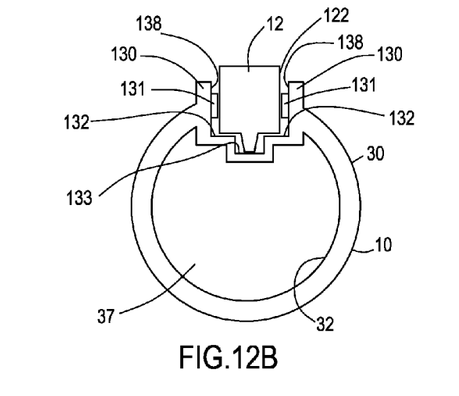
Figure 12C:
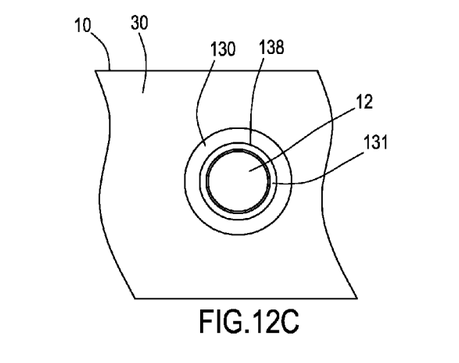
Figure 13:
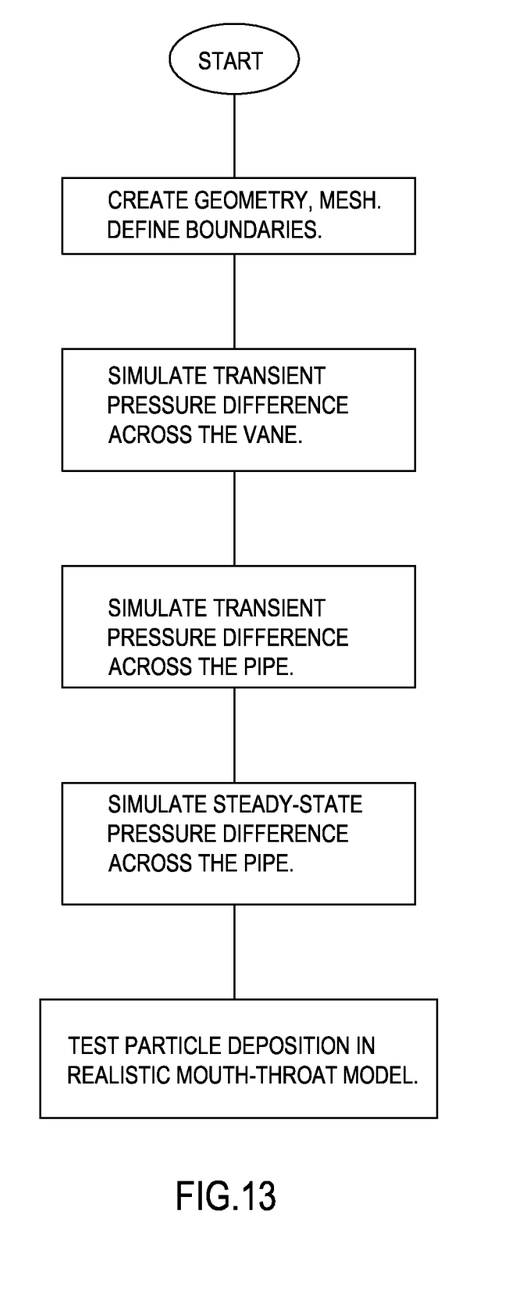
FIG. 13 provides a flowchart showing steps in the design stage of forming an exemplary inhalation airflow regulation device of the present invention as discussed in the Example section below.

Any of the above-described exemplary inhalation airflow regulation devices may further comprise a medication canister connector operatively adapted and sized to receive and utilize a medicine canister. FIGS. 12A-12C provide various views of an exemplary medication canister connector of an exemplary inhalation airflow regulation device. As shown in FIG. 12A, tubular member 10 comprises exemplary medicine canister connecting member 190 positioned along tubular member 10 (typically, between air flow regulating member 24 and first end 11, when both are present). Exemplary medicine canister connecting member 190 comprises at least one side wall 130. Typically, at least one side wall 130 (i) extends into volume 37 of tubular member 210, (ii) extends above outer surface 30 of tubular member 10, or (iii) both (i) and (ii). Exemplary medicine canister connecting member 190 also comprises a canister activation stop 133 positioned within volume 37 of tubular member 10. Exemplary medicine canister connecting member 190 further comprises a canister movement stop 132 positioned between at least one side wall 131 and canister activation stop 133, and a seal material 131 positioned along at least a portion of an inner surface 138 of at least one side wall 131.

As shown in FIG. 12A, medicine canister 12 is positioned within exemplary medicine canister connecting member 190 so as to be held in place via increased friction between seal material 131 and an outer surface 122 of medicine canister 12. When in an "idle" position, a spray end 123 of medicine canister 12 rests on canister activation stop 133, while a canister shoulder 124 is positioned above canister movement stop 132. To spray, medicine canister 12 is pushed toward canister activation stop 133 so as to activate a spray mechanism (not shown) within medicine canister 12. Medicine canister 12 may be pushed until canister shoulder 124 abuts canister movement stop 132. Typically, a metered amount of medicine is released during a given spray step.

FIG. 12B provides an end view of exemplary medicine canister connecting member 190 as viewed along arrow/direction B shown in FIG. 12A. FIG. 12C provides a top view of exemplary medicine canister connecting member 190 as viewed from above medicine canister 12.

The present invention is also directed to methods of making inhalation airflow regulation devices. In one exemplary embodiment, the method of making an inhalation airflow regulation device comprises forming a tubular member (e.g., tubular member 10) having a first end (i.e., first end 11) and an opposite second end (i.e., second end 13), a mouthpiece (i.e., mouthpiece 14) positioned proximate the first end, a first air inlet (i.e., first air inlet 18) positioned proximate the second end, and a medication inlet (i.e., medication inlet 22) positioned along the tubular member between the mouthpiece and the first air inlet; and positioning an air flow regulating member (i.e., exemplary air flow regulating member 24) along the tubular member, the air flow regulating member regulating air flow that passes thru the tubular member. Typically, the air flow regulating member (i.e., exemplary air flow regulating member 24) is positioned between the medication inlet and the first air inlet, but can be present at any location along the tubular member.

The step of forming a tubular member (e.g., tubular member 10) may comprise a single molding step or multiple molding steps (e.g., to form tubular member portion $10_A$ and tubular member portion $10_B$, as well as overlapping member 50). The step of positioning an air flow regulating member (i.e., exemplary air flow regulating member 24) along the tubular member may comprise attaching the air flow regulating member to an inner surface of the tubular member (i.e., inner surface 32) or sandwiching the air flow regulating member between outer edges of two portions of a given tubular member (e.g., between outer edges of two portions of tubular member portion $10_A$ and tubular member portion $10_B$).

The methods of making an inhalation airflow regulation device may further comprise one or more additional steps. Suitable additional steps include, but are not limited to, utilizing or developing a mathematical/computational model in an attempt to better understand fluid flow thru an inhalation airflow regulation device and into a user's lungs; utilizing the mathematical model to design an inhalation airflow regulation device and an air flow regulating member so as to maximize an amount of medicine within an air flow stream reaching a user's lungs from an inhalation airflow regulation device; cutting one or more air flow regulating member portions from a sheet of material; assembling tubular member components and one or more air flow regulating member components; molding a separate mouthpiece component; attaching the mouthpiece component to the first end of the tubular member; attaching a medicine canister (e.g., medicine canister 12) to the tubular member; forming a kit comprising one or more inhalation airflow regulation device components and one or more attachable medicine canisters; and packaging any of the above-mentioned components.

In another exemplary method of making an inhalation airflow regulation device, the exemplary method comprises forming a tubular member (e.g., tubular member 10) having a first end (e.g., first end 11) and an opposite second end (e.g., second end 13), a mouthpiece (e.g., mouthpiece 14) positioned proximate the first end, a first air inlet (e.g., first air inlet 18) positioned proximate the second end, and a medication inlet (e.g., medication inlet 22) positioned along the tubular member between the mouthpiece and the first air inlet; and positioning an air flow regulating member (i.e., exemplary air flow regulating member 24) along the tubular member, the air flow regulating member comprising one or more sheets of material (e.g., single sheet 27 or sheets of material $24_A$ and $24_B$) (i) positioned substantially perpendicular to a direction of air flow thru the tubular member, (ii) secured to the tubular member so as to block at least a portion of an air flow cross-sectional area of the tubular member, and (iii) secured to the tubular member so as to move within the tubular member in response to a threshold amount of an inhalation force applied thereon. As discussed above, typically, the air flow regulating member (i.e., exemplary air flow regulating member 24) is positioned between the medication inlet and the first air inlet. Further, the air flow regulating member (i.e., exemplary air flow regulating member 24) is typically secured to the tubular member so as to block a portion, but not all, of the air flow cross-sectional area to as to allow two-way air flow thru the tubular member at a first location (e.g., first location 39).

The present invention is even further directed to methods of using inhalation airflow regulation devices described herein.

The inhalation airflow regulation devices and inhalers formed therefrom provide improved, controlled air flow when used in combination, for example, with a pressurized metered dose inhaler (PMDI) with the intent of limiting the speed of the inhalation air flow through a given device to increase the medicine particle deposition in the patient's lungs. The present invention is described above and further illustrated below by way of examples, which are not to be construed in any way as imposing limitations upon the scope of the invention. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Studies were performed to predict the behavior of air flow in response to two different flow controller designs. ANSYS CFX was used to create a model of each design and perform tests on the flow controllers computationally. The software was able to model the response of flexible materials to pressure difference or fluid flow. Each design was tested with pressure difference applied to mimic a normal human breathing pattern and a breathing pattern during an asthma attack. The pressure caused a flow controller vane to bend and deflect, resulting in a greater open area at the highest pressure. The resultant open area was compared to an optimal open area that would restrict flow to resemble a normal breathing pattern. The volumetric flow rate was also determined at various inhalation pressure differences and was compared to a desired rate.

Additional testing was performed to compare the results of the mouth/throat particle deposition (MTPD) in a simple tube model against a more realistic model. Four volumetric flow rates were tested with three particle sizes: 1, 5, and 10 micron diameter aerosol particles. The flow rates were based upon peak and average flow rates of normal and asthma attack cases. The results confirmed that greater flow rates and particle size increase the amount of MTPD.

Prototype models of two different flow controller designs (i.e., air flow regulating members 24 as shown in FIGS. 3-4) were then constructed. The material selected for each vane was a 1/32 inch thick commercial-grade neoprene rubber. The small, simple design and low cost allowed for several prototypes to be constructed and tested in parallel with computational simulations to determine the best vane shape to limit flow rate to the desired level. The chosen design was a one-vane, flexible membrane which blocked the upper half of a pipe. Once a final model was chosen and constructed, various tests were run to ensure that it not only performed as desired but also guaranteed that it was safe to use.

Flow rates were measured using a TSI Mass Flowmeter interfaced with Labview. The test results showed that the flow controller could limit asthmatic flow rate as much as 59.83%, reduce MTPD in the upper respiratory regions, and predictably enhance drug delivery in the deeper airways.

In order to create and test the device, two types of studies were conducted. Computer simulations were used to test different vane models to provide predictions of the effectiveness of the device based upon normal and asthma attack breathing patterns. Physical prototypes were also built and tested using equipment such as the TSI Mass Flowmeter. A description of the computational simulations, construction process, and test plan will be discussed below.

A. Simulations

The simulations were conducted following the progression described in the flowchart shown in FIG. 13.

Two different vane types were considered as options for the final device. The first model, Vane 1, shown in FIG. 3, blocks half of the pipe and has a semicircular vane. The second model, Vane 2, shown in FIG. 4, has two separate flaps that attach on one side of the pipe.

Geometries were created for each vane and pipe using ANSYS Design Modeler. The geometry for Vane 1 was generated using only one quarter of pipe, in which the straight edge of the vane closest to the covered half was a fixed support and the other straight edge represented symmetry. The diameter of the pipe was 20 mm, and the diameter of the vane was 19.08 mm. The diameter of the vane was chosen based upon the optimal open area at the lowest pressure difference across the pipe to cause the least amount of particle deposition in the throat. The thickness of the vane was varied in different tests. For the first simulations, the pipe was suppressed and only the vane was considered. A mesh was created for the geometry and was loaded into ANSYS CFX. The vane was defined as being Flexible Dynamic with neoprene rubber material properties. The properties of the neoprene rubber used in construction were not available from the supplier, so the standard neoprene rubber properties in ANSYS were used. The fixed support and the symmetry locations were defined. The other faces of the vane were considered to be a fluid-solid interface, in which the fluid was air surrounding the vane, and the solid was the neoprene rubber of the vane. A negative pressure was applied to one face of the vane, which represented the inhalation. A transient simulation was set up, in which the movement was pressure driven. Under these conditions, the amount of directional deformation along the length of the pipe and deformation in the direction of the radius of the pipe were graphed against the amount of pressure applied. The highest amount of deformation occurred during the highest pressure application. Based upon these deformation dimensions, the amount of open area during the highest pressure could be calculated and compared to the optimal open area at that pressure difference.

The same procedure was performed upon Vane 2 in order to find the deflection needed to achieve the desired open area. During this time, experiments were being performed on the prototype of this model. Experimentation indicated that this design was not as effective in limiting air flow rate, so further study on this vane shape was temporarily suspended.

The next step was to perform a transient analysis on the air flow through the entire pipe using Vane 1 geometry. This analysis would solve for the volumetric fluid flow through the pipe. The resulting data could, in turn, be compared to the optimal flow rate derived from the hybrid breathing curve which was formulated as a suppression of the asthma attack breathing curve to fit the normal. In this case, the vane was suppressed and the body of the pipe was used. In ANSYS, the pipe was divided into three domains. The first domain was the mouth piece, which is the side through which the person would inhale. The middle section was the controller domain. This is the portion of the pipe that contains the vane. The third part of the pipe was the open end that would allow air to enter during the inhalation. As before, the walls, fluid-solid interface, and symmetry were defined. The fluid flowing through the pipe was set to be air at 25° C. The initial conditions were set so that the mouth side would apply a negative pressure (inhalation) following the pressure differences defined in the asthma attack breathing curve. The opening at the opposite end had a pressure of 0 Pascals. The transient analysis was defined; however, when the simulation ran, the mesh at the location of the vane was deformed to the point that a negative volume was created. Obviously, this generated an error, so an alternate method was necessary to provide the results needed.

In order to bypass the problem with the transient analysis, a steady state case could be defined using the whole pipe. The amount of deformation of the vane, which was already determined, could be used to find an angle of deflection (as if the vane remained unbent), which would approximate the open area at the highest pressure difference. In addition, other angles could be tested to see the flow rate if the vane deflected to that degree. Therefore, the geometry was altered so that the vane was in the pipe at an angle and a new mesh was generated.

At the mouth opening, the highest pressure was applied (and made negative) rather than using the transient data. The other end's opening remained at 0 Pa, and all other boundary conditions remained the same as the transient pipe analysis. This simulation was performed with the vane positioned at different angles of deflection, so the volumetric flow rate (Q) through the pipe was determined at four angles of deflection. In the beginning of this study, the need for this project was justified using a simple mouth/throat model designed by Zhang et al. (Zhang, Y., Chia, T. L., & Finlay, W. H. (2006). Experimental measurement and numerical study of particle deposition in highly idealized mouth-throat models. *Aerosol Science and Technology,* 40(5), 361-372.). Steady state analysis was performed so that three particle sizes (1, 5, and 10 micron diameter aerosol particles) traveled through the model at velocities that mimicked breathing velocities. The purpose of this study was to discover the effect of particle size and velocity on the amount of MTPD rather than lung particle deposition.

The study verified that larger particle size and faster velocities cause greater amounts of MTPD. Recently, a more accurate mouth-throat model was provided by Dr. Kleinstreuer at North Carolina State University. Using this model, similar simulations could be run to determine the legitimacy of the earlier study. In this case, five domains were defined so that MTPD could be quantified in each region: mouth, upper throat, lower throat, epiglottis, and trachea. The inlet was defined as the opening of the mouth, and the outlet was the end of the trachea. In this simulation, the inlet velocity was the condition of the flow, not pressure difference. Four velocities were tested: the maximum and average velocities of asthma attack breathing and normal breathing from the Li et al. study (Li, Z., Kleinstreuer, C., & Zhang, Z. (2007). Particle deposition in the human tracheobronchial airways due to transient inspiratory flow patterns. *Journal of Aerosol Science,* 38, 625-644). Each velocity was tested at each of the three particle sizes tested previously with steady state and no-slip wall conditions. Because the physical and computational tests were being conducted simultaneously, the volumetric flow rate of a subject inhaling quickly (like an asthma attack breath) uninhibited then through the device were able to be applied to the realistic mouth-throat model. Therefore, experimental data could be tested to determine the actual effectiveness of the physical flexible vane at reducing MTPD.

B. Construction

Prototypes were constructed of the vane types alongside the computational work to select the best design for controlling the air flow rate. The materials and methods used in construction and the prototypes constructed are described below.

Materials

The materials used to build the prototype models (having a construction as shown in FIG. 5) are listed below.

PVC piping (¾" outer diameter)

PVC coupling (¾")

Commercial Grade Neoprene Rubber (1/32" thickness)

Scissors

Ruler

Super Glue/Industrial Epoxy

Pipe Clamp
Compass
180-Grit Sandpaper The PVC piping was chosen as the material for the pipe instead of 3D printing the pipe. The rougher surface of a pipe created by 3D printing may have disturbed airflow through the pipe compared to the smooth surface of a PVC pipe. Neoprene rubber was chosen as the material for the flexible membrane due to its high durability, flexibility, and the availability in many thicknesses. The smallest thickness of commercial grade neoprene rubber, 1/32 of an inch, was purchased early in the design phase and proved to be the only product needed due to its ability to limit the air flow rate to the optimal rate.

Working Designs

The first prototype was built using the Vane 2 design for the rubber. The rubber was initially cut using an X-acto Knife, for precision. This method of cutting caused the rubber to have a jagged edge, however, which would potentially be disruptive to the flow. The Vane 2 design was eliminated after testing due to the fact that it did not sufficiently restrict air flow.

The second prototype was built using the Vane 1 design for the rubber using the X-acto Knife. This model was constructed to test the vane shape alone and was not cut to the exact dimensions necessary for significant air flow restriction. There was too much open area in this model.

The third and final models were built using the Vane 1 design for the rubber. This design for the rubber is the most restrictive because it has the highest surface area possible, so that it will not deflect as much as the Vane 2. The final design was built using the minimum open area, 22.06 mm$^2$, determined from computational analysis.

Methods

Construction of a model began with cutting and preparing the PVC piping. The PVC pipe was cut into 4 inch sections using a miter saw. The ends of the piping were then smoothed using a lathe to ensure a smooth contact surface for creating a tight seal and for safety and comfort when testing. This was necessary because a person would be placing his or her mouth around one end of the pipe. A metal file was used to further smooth out the ends of the pipe. In order to interface the TSI Flowmeter, which was used in testing, and the PVC pipe, a one inch section on inner surface of one end of the PVC pipe was filed down using the lathe. The surface was filed just enough to ensure a tight fit between the flowmeter and the pipe.

The PVC pipe coupling initially had a ridge on the inside surface, halfway through the length of the piece. This ridge needed to be removed by filing down the inner surface using a lathe. The outer diameter and inner diameter of the PVC pipe were measured to be 26.5 mm and 20.5 mm, respectively.

A circle of diameter 26.5 mm was drawn on the rubber using a compass. A circle of radius 10.25 mm (R2) was drawn concentric to the first circle. The area of the rubber flap, 142.94 mm$^2$, was determined by subtracting the minimum open area from half of the open area of the inner pipe, 165 mm$^2$. The radius of the flap 9.54 mm was used to draw a semi-circle on the rubber adjacent to the fixed area of rubber which blocks off half of the open area of the pipe. The outer circle was cut out using scissors and then the edge between the inner circle and the rubber flap was cut to create the minimum open area. The rubber edge was glued on both sides to a 4 inch piece of PVC pipe with either epoxy or super glue and was assembled as shown in FIG. 5.

The PVC coupling was used to cover the connection between the two four-inch sections of pipe and the rubber to ensure no air leakage at this seal. A pipe clamp secured the device and applied pressure to the connection during the glue drying process. Any material that needed to be further filed away from the surface of the inlet/outlet of the PVC piping was removed using 180-grit fine sandpaper. The final model is as shown in FIG. 5.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An inhalation airflow regulation device suitable for use with one or more inhaler components, said inhalation airflow regulation device comprising:
    a tubular member having a first end, an opposite second end, and an air flow cross-sectional area between said first end and said opposite second end;
    an air outlet positioned proximate said first end;
    a first air inlet positioned proximate said opposite second end;
    an air flow regulating member positioned along said tubular member, said air flow regulating member comprising one or more coplanar sheets of material (i) positioned at a first location within said tubular member, (ii) secured to said tubular member so as to block a portion, but not all, of said air flow cross-sectional area so as to allow two-way air flow thru said tubular member at the first location, and (iii) secured to said tubular member so that at least a portion of said one or more coplanar sheets of material moves toward said first end within said tubular member in response to a threshold amount of an inhalation force applied thereon; and
    a medication inlet positioned along said tubular member between said air outlet and said first air inlet; said air flow regulating member being positioned along said tubular member between said medication inlet and said first air inlet so as to regulate air flow that passes thru said tubular member and by said medication inlet.

2. The inhalation airflow regulation device of claim 1, further comprising a connecting member proximate said air outlet, said connecting member being operatively adapted to connect to an air inlet of a separate inhaler component.

3. The inhalation airflow regulation device of claim 2, wherein said separate inhaler component comprises one or more components selected from a second tubular member, a second tubular member mouthpiece, a second tubular member medication inlet, a second tubular member canister connection member, and a medicine canister.

4. The inhalation airflow regulation device of claim 1, further comprising a mouthpiece positioned proximate said first end.

5. An inhalation airflow regulation device suitable for use with one or more inhaler components, said inhalation airflow regulation device comprising:
    a tubular member having a first end and an opposite second end;
    a mouthpiece positioned proximate said first end;
    a first air inlet positioned proximate said opposite second end;
    a medication inlet positioned along said tubular member between said mouthpiece and said first air inlet; and
    an air flow regulating member positioned at a first location along said tubular member within a plane between said medication inlet and said first air inlet, said air flow regulating member regulating air flow that passes thru an air flow cross-sectional area of said tubular member and by said medication inlet; and wherein said air flow regulating member comprises one or more coplanar sheets of material (i) positioned at said first location within said tubular member, (ii) secured to said tubular member so as to block at least a portion of an air flow cross-sectional area of said tubular member, and (iii) secured to said tubular member so that at least a portion of said one or more coplanar sheets of material moves out of said plane toward said first end within said tubular member in response to a threshold amount of an inhalation force applied thereon.

6. The inhalation airflow regulation device of claim 5, wherein said air flow regulating member is secured to said tubular member so that at least a portion of said one or more coplanar sheets of material moves out of said plane toward said second end within said tubular member in response to a threshold amount of an exhalation force applied thereon.

7. The inhalation airflow regulation device of claim 5, wherein said air flow regulating member comprises one or more coplanar sheets of elastic material, at least a portion of each of said one or more coplanar sheets of elastic material is attached to said tubular member at said first location, and an outer peripheral edge of each of said one or more coplanar sheets of elastic material is positioned within said air flow cross-sectional area at said first location and spaced a distance from an inner surface of said tubular member.

8. The inhalation airflow regulation device of claim 5, wherein said air flow regulating member comprises one or more coplanar sheets of neoprene, at least a portion of each of said one or more coplanar sheets of neoprene is attached to said tubular member at said first location, and an outer peripheral edge of each of said one or more coplanar sheets of neoprene is positioned within said air flow cross-sectional area at said first location and spaced a distance from an inner surface of said tubular member.

9. The inhalation airflow regulation device of claim 5, wherein said air flow regulating member blocks from 75 to 95% of said air flow cross-sectional area at the first location.

10. The inhalation airflow regulation device of claim 5, wherein said tubular member comprises a single tube.

11. The inhalation airflow regulation device of claim 5, wherein said tubular member comprises two separate tubular member portions, said air flow regulating member being positioned between said two separate tubular member portions.

12. The inhalation airflow regulation device of claim 11, further comprising an overlapping tubular member, wherein at least a portion of said overlapping tubular member extends over outer surfaces of each of said two separate tubular member portions.

13. The inhalation airflow regulation device of claim 1, further comprising a medicine canister connecting member positioned along said tubular member between said air flow regulating member and said first end.

14. The inhalation airflow regulation device of claim 13, wherein said medicine canister connecting member comprises at least one side wall (i) extending into a volume of said tubular member, (ii) extending above an outer surface of said tubular member, or (iii) both (i) and (ii), and a canister activation stop positioned within the volume of said tubular member.

15. The inhalation airflow regulation device of claim 14, wherein said medicine canister connecting member further comprises a canister movement stop positioned between said at least one side wall and said canister activation stop, and a seal material along at least a portion of said at least one side wall.

16. The inhalation airflow regulation device of claim 5 in combination with one or more medicine canisters.

17. A method of making the inhalation airflow regulation device suitable for use with one or more inhaler components, said inhalation airflow regulation device comprising: a tubular member having a first end and an opposite second end; a mouthpiece positioned proximate said first end; a first air inlet positioned proximate said opposite second end; a medication inlet positioned along said tubular member between said mouthpiece and said first air inlet; and an air flow regulating member positioned at a first location along said tubular member within a plane between said medication inlet and said first air inlet, said air flow regulating member regulating air flow that passes thru an air flow cross-sectional area of said tubular member and by said medication inlet; and wherein said air flow regulating member comprises one or more coplanar sheets of material (i) positioned at said first location within said tubular member, (ii) secured to said tubular member so as to block at least a portion of an air flow cross-sectional area of said tubular member, and (iii) secured to said tubular member so that at least a portion of said one or more coplanar sheets of material moves out of said plane toward said first end within said tubular member in response to a threshold amount of an inhalation force applied thereon, said method comprising:
  forming the tubular member;
  forming the mouthpiece and positioning the mouthpiece proximate the first end; and
  positioning the air flow regulating member along the tubular member, the air flow regulating member regulating air flow that passes thru the tubular member.

18. A method of using the inhalation airflow regulation device suitable for use with one or more inhaler components, said inhalation airflow regulation device comprising: a tubular member having a first end and an opposite second end; a mouthpiece positioned proximate said first end; a first air inlet positioned proximate said opposite second end; a medication inlet positioned along said tubular member between said mouthpiece and said first air inlet; and an air flow regulating member positioned at a first location along said tubular member within a plane between said medication inlet and said first air inlet, said air flow regulating member regulating air flow that passes thru an air flow cross-sectional area of said tubular member and by said medication inlet; and wherein said air flow regulating member comprises one or more coplanar sheets of material (i) positioned at said first location within said tubular member, (ii) secured to said tubular member so as to block at least a portion of an air flow cross-sectional area of said tubular member, and (iii) secured to said tubular member so that at least a portion of said one or more coplanar sheets of material moves out of said plane toward said first end within said tubular member in response to a threshold amount of an inhalation force applied thereon, said method comprising:
  positioning the inhalation airflow regulation device within a user's mouth; and
  breathing thru the inhalation airflow regulation device.

19. The inhalation airflow regulation device of claim 1, wherein at least a portion of said one or more coplanar sheets of material (i) moves toward said second end within said tubular member in response to a threshold amount of an exhalation force applied thereon, (ii) is attached to said tubular member at said first location, and (iii) an outer peripheral edge of each of said one or more coplanar sheets of material is positioned within said air flow cross-sectional area at said first location and spaced a distance from an inner surface of said tubular member.

* * * * *